US00PP19108P2

(12) United States Plant Patent
Smith

(10) Patent No.: US PP19,108 P2
(45) Date of Patent: Aug. 19, 2008

(54) ***CHRYSANTHEMUM* PLANT NAMED 'SUNNY YOIGLOO'**

(50) Latin Name: *Chrysanthemum×morifolium*
Varietal Denomination: Sunny Yoigloo

(75) Inventor: Mark A. Smith, Fort Myers, FL (US)

(73) Assignee: Yoder Brothers Inc., Barberton, OH (US)

( * ) Notice: Subject to any disclaimer, the term of this patent is extended or adjusted under 35 U.S.C. 154(b) by 0 days.

(21) Appl. No.: 11/705,879

(22) Filed: Feb. 14, 2007

(51) Int. Cl.
*A01H 5/00* (2006.01)

(52) U.S. Cl. ..... Plt./295

(58) Field of Classification Search ..... Plt./295, Plt./289

See application file for complete search history.

*Primary Examiner*—Kent L. Bell
*Assistant Examiner*—June Hwu
(74) *Attorney, Agent, or Firm*—C. A. Whealy

(57) ABSTRACT

A new and distinct cultivar of *Chrysanthemum* plant named 'Sunny Yoigloo', characterized by its upright, outwardly spreading and mounding plant habit; freely branching habit; dense and full plant habit; uniform and freely flowering habit; duplex-type inflorescences with obovate-shaped ray florets; bright yellow-colored ray florets; and natural season flowering about September 18$^{th}$ in the Northern Hemisphere.

1 Drawing Sheet

Botanical designation: *Chrysanthemum×morifolium.*
Cultivar denomination: 'Sunny Yoigloo'.

BACKGROUND OF THE INVENTION

The present invention relates to a new and distinct cultivar of *Chrysanthemum* plant, botanically known as *Chrysanthemum×morifolium,* commercially grown as a perennial garden *Chrysanthemum* and hereinafter referred to by the name 'Sunny Yoigloo'.

The objective of the breeding program is to create new perennial garden-type *Chrysanthemum* cultivars having inflorescences with desirable inflorescence forms, attractive floret colors and good garden performance.

The new *Chrysanthemum* is a naturally-occurring whole plant mutation of the *Chrysanthemum×morifolium* cultivar Warm Yoigloo, disclosed in a U.S. Plant Patent application filed concurrently. The new *Chrysanthemum* was discovered and selected by the Inventor as a single flowering plant within a population of plants of the cultivar Warm Yoigloo in December, 2003, in Alva, Fla. The selection of this plant was based on its desirable inflorescence color and good form and substance.

Asexual reproduction of the new *Chrysanthemum* by vegetative cuttings was first conducted in Alva, Fla. in February, 2004. Asexual reproduction by cuttings has shown that the unique features of this new *Chrysanthemum* are stable and reproduced true to type in successive generations.

SUMMARY OF THE INVENTION

Plants of the cultivar Sunny Yoigloo have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Sunny Yoigloo'. These characteristics in combination distinguish 'Sunny Yoigloo' as a new and distinct garden *Chrysanthemum* cultivar:

1. Upright, outwardly spreading and mounding plant habit.
2. Freely branching habit; dense and full plant habit.
3. Uniform and freely flowering habit.
4. Duplex-type inflorescences with obovate-shaped ray florets.
5. Bright yellow-colored ray florets.
6. Natural season flowering about September 18$^{th}$ in the Northern Hemisphere.

In side-by-side comparisons conducted in Alva, Fla., plants of the new *Chrysanthemum* differed from plants of the parent, the cultivar Warm Yoigloo, in the following characteristics:

1. Plants of the new *Chrysanthemum* flowered later than plants of the cultivar Warm Yoigloo when grown under natural season conditions.
2. Plants of the new *Chrysanthemum* and the cultivar Warm Yoigloo differed in ray floret color as plants of the cultivar Warm Yoigloo had orange bronze-colored ray florets.

Plants of the new *Chrysanthemum* can be compared to plants of the *Chrysanthemum* cultivar MN98-M91-1, disclosed in U.S. Plant Pat. No. 15,027. In side-by-side comparisons conducted in Alva, Fla., plants of the new *Chrysanthemum* differed from plants of the cultivar MN98-M91-1 in the following characteristics:

1. Plants of the new *Chrysanthemum* were smaller, fuller and more mounded than plants of the cultivar MN98-M91-1.
2. Plants of the new *Chrysanthemum* flowered more uniformly than plants of the cultivar MN98-M91-1.
3. Plants of the new *Chrysanthemum* had smaller inflorescences with more ray florets than plants of the cultivar MN98-M91-1.
4. Plants of the new *Chrysanthemum* flowered about 10 to 14 days later than plants of the cultivar MN98-M91-1 when grown under natural season conditions.

BRIEF DESCRIPTION OF THE PHOTOGRAPHS

The accompanying photographs illustrate the overall appearance of the new *Chrysanthemum.* These photographs show the colors as true as it is reasonably possible to obtain in colored reproductions of this type. Colors in the photographs may differ slightly from the color values cited in the detailed botanical description which accurately describe the colors of the new *Chrysanthemum.*

The photograph at the bottom of the sheet comprises a side perspective view of a typical flowering plant of 'Sunny Yoigloo'.

The photograph at the top of the sheet is a close-up view of typical inflorescences of 'Sunny Yoigloo'.

DETAILED BOTANICAL DESCRIPTION

The aforementioned photographs and following observations and measurements describe plants grown in Pendleton, S.C. during the summer in an outdoor nursery and under conditions and practices which approximate those generally used in commercial garden *Chrysanthemum* production. During the production of the plants, day temperatures averaged 32° C. and night temperatures averaged 21° C. Plants were grown in 20 cm-containers under natural season conditions. Plants used in the photographs and for the description were about four months old. In the following description, color references are made to The Royal Horticultural Society Colour Chart, 1995 Edition, except where general terms of ordinary dictionary significance are used.

Botanical classification: *Chrysanthemum×morifolium* cultivar Sunny Yoigloo.

Parentage: Naturally-occurring whole plant mutation of the *Chrysanthemum×morifolium* cultivar Warm Yoigloo, disclosed in a U.S. Plant Patent application filed concurrently.

Propagation:

*Type.*—Terminal vegetative cuttings.

*Time to initiate roots.*—About four days at temperatures of about 21° C.

*Time to produce a rooted young plant.*—About ten to twelve days at temperatures of about 21° C.

*Root description.*—Fine, fibrous; white in color.

*Rooting habit.*—Freely branching.

Plant description:

*Appearance.*—Perennial duplex-type garden *Chrysanthemum.* Stems upright and outwardly spreading giving a uniformly mounded appearance to the plant. Freely branching habit, about nine to ten lateral branches each with multiple secondary and tertiary branches; pinching is not required; dense and full plant habit. Strong and vigorous growth habit.

*Plant height.*—About 30 cm.

*Plant width.*—About 62 cm.

*Lateral branches.*—Length: About 28 cm. Diameter: About 8 mm. Internode length: About 2.5 cm. Strength: Strong. Texture: Pubescent. Color: 147B.

*Leaves.*—Arrangement: Alternate, simple. Length: About 4.2 cm. Width: About 2.4 cm. Apex: Cuspidate to mucronate. Base: Attenuate. Margin: Palmately lobed, sinuses between lateral lobes parallel to convergent. Texture, upper and lower surfaces: Pubescence; veins prominent on lower surface. Color: Developing foliage, upper surface: 137A. Developing foliage, lower surface: 137B. Fully expanded foliage, upper surface: 137A; venation, 137C. Fully expanded foliage, lower surface: 137C; venation, 137C. Petiole: Length: About 9 mm. Diameter: About 3 mm. Texture, upper and lower surfaces: Pubescent. Color, upper and lower surfaces: 137C.

Inflorescence description:

*Appearance.*—Duplex-type inflorescence form with obovate-shaped ray florets. Inflorescences borne on terminals above foliage. Disk and ray florets arranged acropetally on a capitulum. Inflorescences fragrant, typical of *Chrysanthemum.*

*Flowering response.*—Under natural season conditions, plants flower about September 18$^{th}$ in the Northern Hemisphere.

*Postproduction longevity.*—Inflorescences maintain good color and substance for about four weeks in an outdoor nursery. Inflorescences persistent.

*Quantity of inflorescences.*—About 88 inflorescences develop per lateral branch.

*Inflorescence bud.*—Height: About 1.2 cm. Diameter: About 1.4 cm. Shape: Oblate. Color: 7C.

*Inflorescence size.*—Diameter: About 3.8 cm. Depth (height): About 1.5 cm. Disc diameter: About 5 mm. Receptacle height: About 5 mm. Receptacle diameter: About 1.7 cm.

*Ray florets.*—Shape: Obovate. Orientation: Initially upright, then about 90° from vertical; eventually reflexing. Aspect: Initially incurved, then mostly flat. Length: About 1.7 cm. Width: About 5 mm. Apex: Emarginate. Base: Acute. Margin: Entire. Texture, upper and lower surfaces: Smooth, glabrous; longitudinally ribbed. Number of ray florets per inflorescence: About 280 arranged in about 18 to 19 whorls. Color: When opening, upper surface: 8A. When opening, lower surface: 8C. Fully opened, upper surface: Outer ray florets, 8A, becoming close to 12B with development, inner ray florets, 12A. Fully opened, lower surface: Outer ray florets, 8C; inner ray florets, 12A.

*Disc florets.*—Shape: Tubular, elongated. Length: About 2 mm. Diameter: Less than 1 mm. Number of disc florets per inflorescence: About 107. Color, immature: Apex: Close to 7A. Mid-section: Close to 7D. Base: Close to 1D. Color, mature: Apex: Close to 163B. Mid-section: Close to 162B. Base: Close to 157A.

*Phyllaries.*—Number of phyllaries per inflorescence: About 28 arranged in about five whorls. Length: About 6 mm. Width: About 3 mm. Shape: Elliptical. Apex: Acute. Base: Truncate. Texture, upper surface: Smooth, glabrous. Texture, lower surface: Pubescent. Color, upper surface: Close to 144A. Color, lower surface: Close to 146B.

*Peduncles.*—Length: About 6.1 cm. Diameter: About 1 mm. Angle: Mostly upright or curving upright. Strength: Strong. Texture: Pubescent. Color: Close to 191A.

*Reproductive organs.*—Androecium: None observed on disc florets. Gynoecium: Present on both ray and disc florets. Pistil length: About 6 mm. Stigma shape: Bi-parted. Stigma color: Close to 10B. Style length: About 3 mm. Style color: Close to 10D. Ovary color: Close to 157D.

*Seed/fruit.*—Seed and fruit production has not been observed.

Disease/pest resistance: Resistance to pathogens and pests common to *Chrysanthemums* has not been observed on plants grown under commercial conditions.

Garden performance: Plants of the new *Chrysanthemum* have demonstrated excellent garden performance and will overwinter in USDA Zones 5 and higher; plants of the new *Chrysanthemum* have been observed to tolerate high temperatures of about 38° C.

It is claimed:

1. A new and distinct *Chrysanthemum* plant named 'Sunny Yoigloo' as illustrated and described.

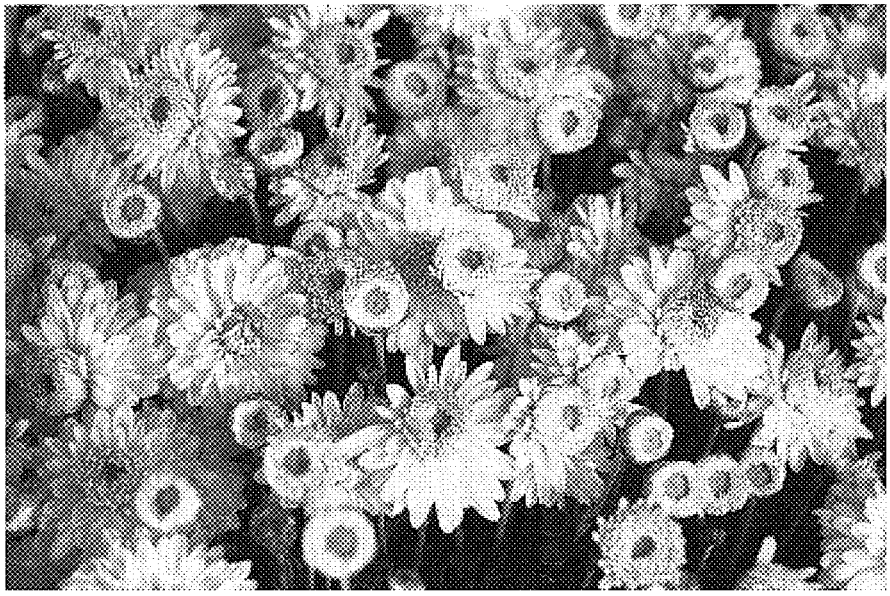
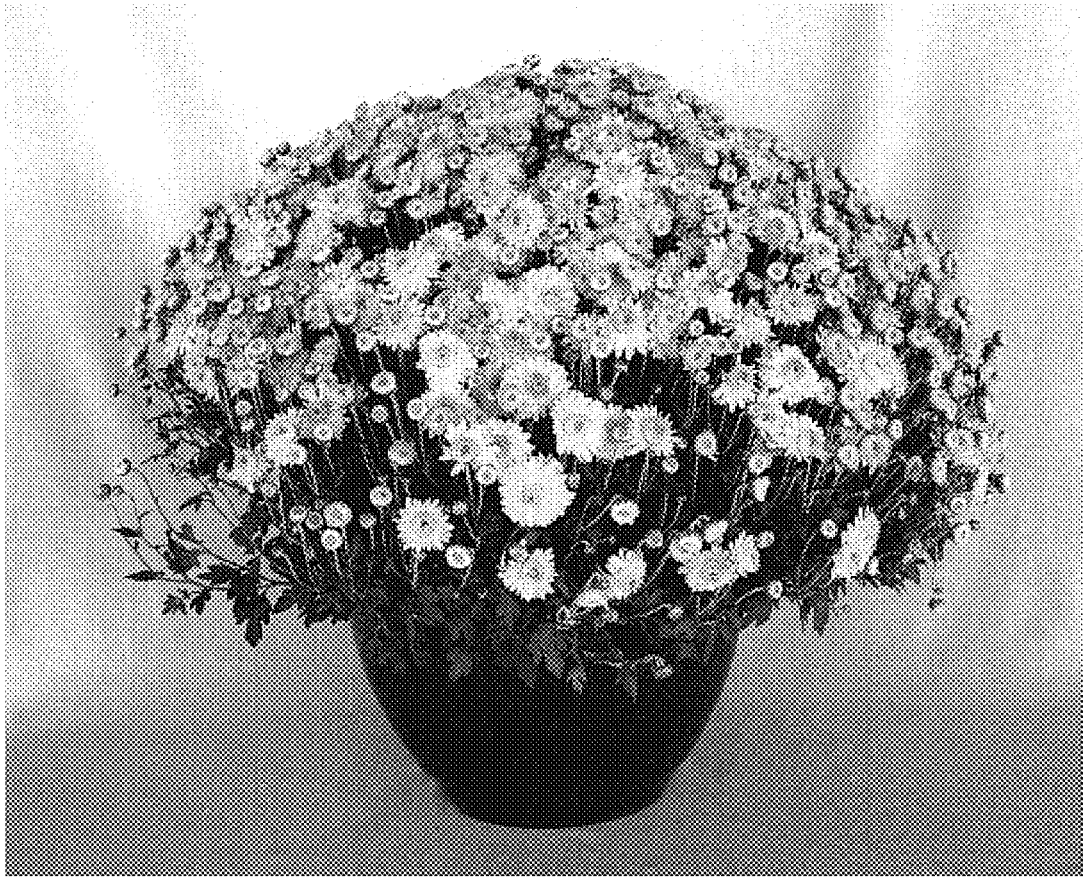

* * * * *